United States Patent [19]

Nishikata et al.

[11] Patent Number: 5,659,085

[45] Date of Patent: Aug. 19, 1997

[54] CYCLOBUTENEDIONE DERIVATIVE, PROCESS FOR PREPARING THE SAME, AND NONLINEAR OPTICAL ELEMENT

[75] Inventors: Yasunari Nishikata; Lyong Sun Pu, both of Ebina, Japan

[73] Assignee: Fuji Xerox Co., Ltd., Tokyo, Japan

[21] Appl. No.: 421,876

[22] Filed: Apr. 14, 1995

[30] Foreign Application Priority Data

May 20, 1994 [JP] Japan .................................. 6-107038

[51] Int. Cl.$^6$ .................................................. C07C 211/35
[52] U.S. Cl. .................................. 564/307; 257/40
[58] Field of Search ............................ 564/307, 502; 257/40

[56] References Cited

U.S. PATENT DOCUMENTS

| | | | |
|---|---|---|---|
| 4,986,935 | 1/1991 | Ageishi et al. | 252/587 |
| 5,106,997 | 4/1992 | Pu | 548/532 |
| 5,210,302 | 5/1993 | Pu | 564/307 |

FOREIGN PATENT DOCUMENTS

| | | |
|---|---|---|
| 1-204031 | 8/1989 | Japan . |
| 2-259735 | 10/1990 | Japan . |
| 3-71117 | 3/1991 | Japan . |
| 3-112950 | 5/1991 | Japan . |
| 3-112961 | 5/1991 | Japan . |
| 4-199135 | 7/1992 | Japan . |
| 4-202165 | 7/1992 | Japan . |
| 4-202166 | 7/1992 | Japan . |
| 4-202167 | 7/1992 | Japan . |
| 5-229999 | 9/1993 | Japan . |
| 5-281587 | 10/1993 | Japan . |
| 5-310655 | 11/1993 | Japan . |
| 6-82857 | 3/1994 | Japan . |
| 6-100511 | 4/1994 | Japan . |
| 6-175178 | 6/1994 | Japan . |
| 6-306027 | 11/1994 | Japan . |

Primary Examiner—Brian M. Burn
Attorney, Agent, or Firm—Oliff & Berridge

[57] ABSTRACT

The present invention provides a novel chemical substance suitable for practical organic nonlinear optical element having a high nonlinear optical effect, a process for the preparation thereof, and a nonlinear optical element prepared from such a chemical substance. A novel cyclobutenedione derivative prepared in accordance with the following reaction formula, a process for the preparation thereof, and a nonlinear optical element comprising such a derivative are provided:

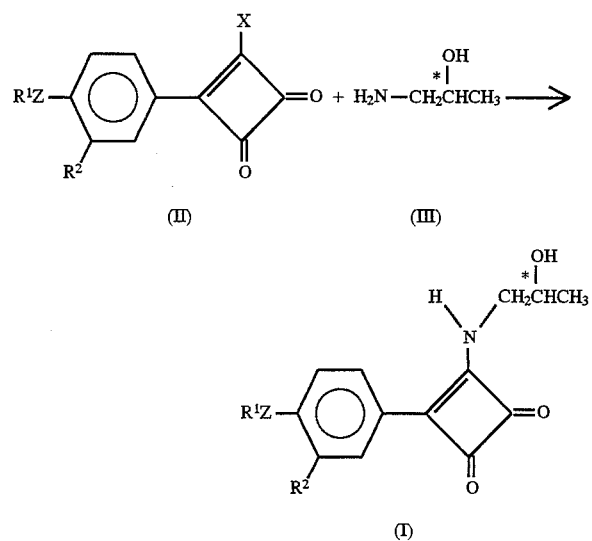

wherein Z represents an oxygen atom or a sulfur atom; $R^1$ represents an alkyl group, an alkenyl group or an alkynyl group; $R^2$ represents a hydrogen atom, an alkyl group, an alkenyl group or an alkynyl group; and C* represents an asymmetric carbon atom, with the proviso that $R^1$ and $R^2$ may be connected to each other to form a methylene chain and that the hydrogen atom(s) in $R^1$ may be substituted by a halogen atom, an alkyloxy group or a cyano group.

2 Claims, 1 Drawing Sheet

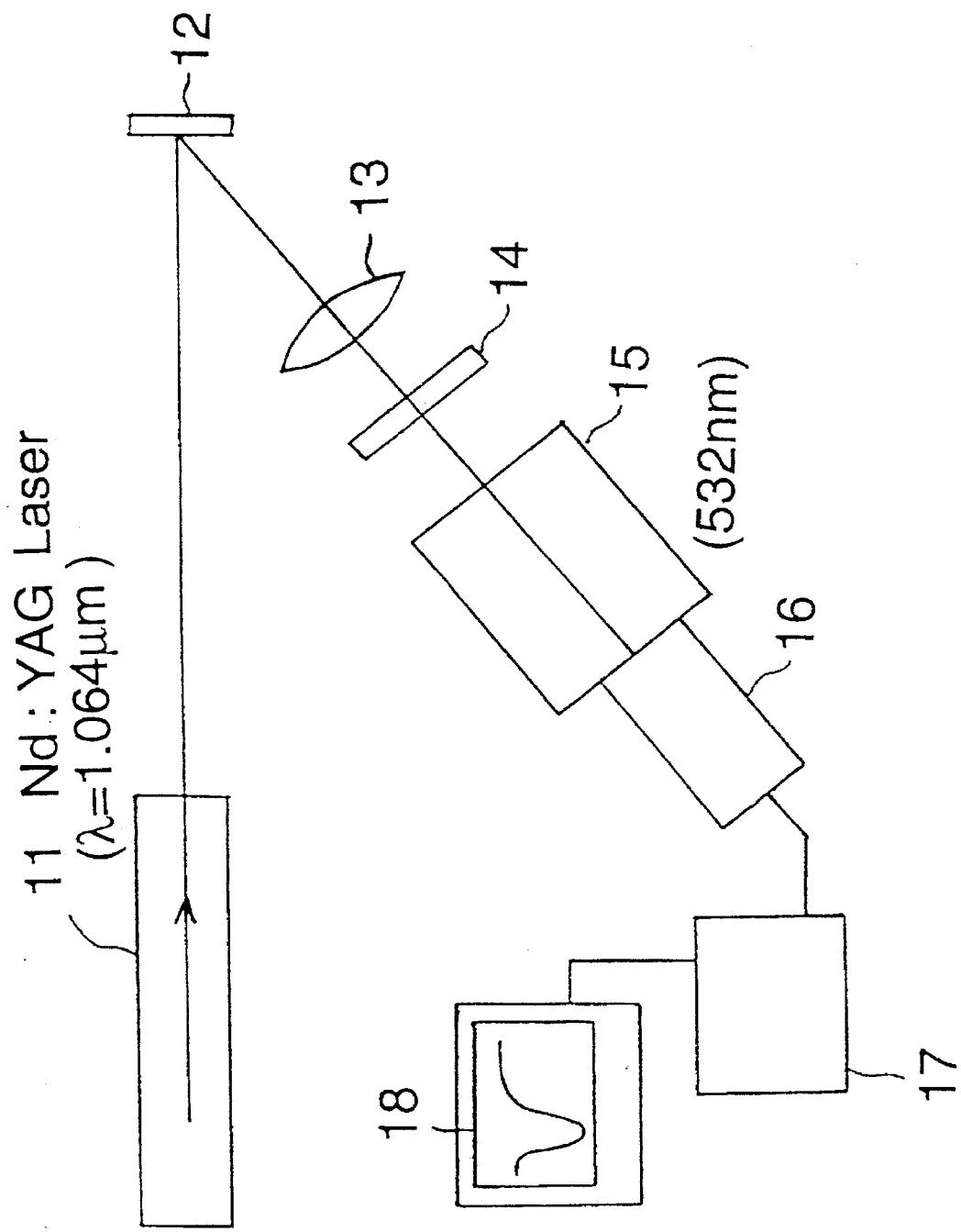

CYCLOBUTENEDIONE DERIVATIVE, PROCESS FOR PREPARING THE SAME, AND NONLINEAR OPTICAL ELEMENT

FIELD OF THE INVENTION

The present invention relates to a novel cyclobutenedione derivative which can be used as a nonlinear optical material. More particularly, the present invention relates to a process for the preparation of such a cyclobutenedione derivative. The present invention further relates to a nonlinear optical element comprising such a cyclobutenedione derivative.

BACKGROUND OF THE INVENTION

A nonlinear optical element plays an important role in the field of optical communications and optical information processing. A nonlinear optical material for nonlinear optical element is a substance which exerts extremely important effects in the processing of optical signal. For example, it can exert an-optical mixing effect to generate a frequency representative of the sum or difference of two incident lights having different frequencies. It also exerts an optical parametric effect to emit light having a frequency different from the original frequency. It further exerts Pockels effect or Kerr effect due to the change in the refractive index of light medium. Further, it can convert incident light into second harmonic (SHG) or third harmonic (THG). Moreover, it exerts a memory effect due to optical bistability.

As the nonlinear optical element material there has heretofore been mainly used an inorganic compound. As such an inorganic nonlinear optical material there has been known an inorganic compound such as potassium titanium phosphate (KTP: $KTiOPO_4$) and lithium niobate (LN: $LiNbO_3$) in crystal form. However, one of these inorganic compounds can satisfy the requirements in the foregoing applications.

On the other hand, an organic nonlinear optical material has recently been noted as a new optical element material in the field of optoelectronics and extensively studied. In particular, it has been known that a compound having an electron donative group and an electron attractive group in π-electron conjugated system undergoes an interaction between laser beam as electromagnetic wave and π-electron unevenly distributed in the molecule to exhibit a strong optical nonlinearity at the molecular level (on a molecular basis).

Examples of compounds which have been studied include 2-methyl-4-nitroaniline, m-nitroaniline, N-(4-nitrophenyl)-L-prolinol, 4-dimethylamino-4'-nitrostilbene, and 4'-nitrobenzylidene-4-nitroaniline.

Most of these materials are used in the form of single crystal similarly to the inorganic materials. These single crystals need to be noncentrosymmetric to exert secondary optical nonlinearity effect. However, since these materials have a high molecular dipole moment, the noncentrosymmetric crystals can hardly form a thermodynamically stable phase.

Referring to the design of a material which forms an noncentrosymmetric crystal, the introduction of asymmetric centers or the use of hydrogen bonds has been known useful. However, ordinary methods have not been found yet.

Further, problems characteristic of organic materials, i.e., difficulty in crystal growth and fragility of the resulting crystal, make it difficult to precision-process these crystals. It has thus been keenly desired to put into practical use of a high performance material necessary for the preparation of high efficiency elements.

In general, a nonlinear optical element is required to exhibit a high optical nonlinearity, an excellent workability, heat resistance, weathering stability and optical transparency, and a high breakdown voltage and stability upon irradiation with laser beam in combination. However, among known materials, nothing has been put into practical use to satisfy these requirements.

The inventors previously proposed cyclobutenedione derivatives represented by the general formula (IV) shown below and nonlinear optical elements comprising these cyclobutenedione derivatives (see JP-A-3-112950 (The term "JP-A" as used herein means an "unexamined published Japanese patent application")). These derivatives are characterized by optical nonlinearity extremely greater than that of known materials. However, these derivatives are disadvantageous in that they are difficultly soluble in various solvents and have a high melting point (254° C. to 256° C.) as viewed from the temperature range suitable for melt working. It has thus been desired to provide a material having a better workability.

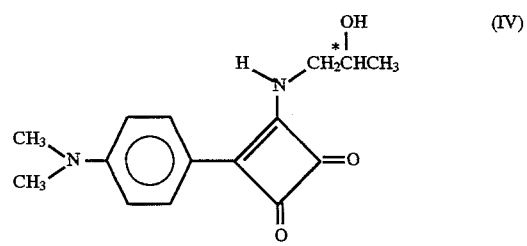

(IV)

SUMMARY OF THE INVENTION

It is therefore an object of the present invention to provide a novel chemical substance suitable for the preparation of a practical organic nonlinear optical element, which has a high nonlinear optical effect, which has an excellent chemical and thermal stability, and transparency, and which is apt to crystallize and process from liquid phase and melt phase.

It is another object of the present invention to provide a process for the preparation of such a chemical substance.

It is a further object of the present invention to provide a nonlinear optical element prepared from such a material.

These and other objects of the present invention will become more apparent from the following detailed description and examples.

The inventors have found that the introduction of appropriate substituents into a compound having a high molecular dipole moment which can easily form a centrosymmetric structure upon crystallization makes it possible to obtain a compound having a high secondary nonlinear optical effect and confirmed that the resulting compound can be applied to organic nonlinear optical elements. Thus, the present invention has been worked out.

The first aspect of the present invention is a cyclobutenedione derivative, represented by the following general formula (I)

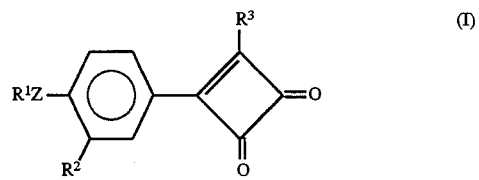

(I)

wherein Z represents an oxygen atom or a sulfur atom; $R^1$ represents an alkyl group (preferably having 1 to 18 carbon atoms, more preferably 1 to 12 carbon atoms), an alkenyl group (preferably having 1 to 18 carbon atoms, more preferably 1 to 12 carbon atoms), or an alkynyl group (preferably having 1 to 18 carbon atoms, more preferably 1 to 12 carbon atoms); $R^2$ represents a hydrogen atom, an alkyl group (preferably having 1 to 12 carbon atoms, more preferably 1 to 6 carbon atoms), an alkenyl group (preferably having 1 to 12 carbon atoms, more preferably 1 to 6 carbon atoms), or an alkynyl group (preferably having 1 to 12 carbon atoms, more preferably 1 to 6 carbon atoms); and $R^3$ represents the following substituent:

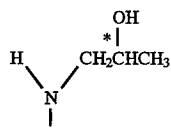

wherein C* represents an asymmetric carbon atom (having R- or S-configuration, preferably having R-configuration), with the proviso that $R^1$ and $R^2$ may be connected to each other to form a methylene chain —$(CH_2)_n$— (in which n represents an integer 1 to 10), and that the hydrogen atom(s) in $R^1$ may be substituted by a halogen atom, an alkyloxy group (preferably having 1 to 12 carbon atoms, more preferably 1 to 6 carbon atoms) or a cyano group.

In formula (I), $R^1$ preferably represents an alkyl group. $R^2$ preferably represents an alkyl group.

The second aspect of the present invention is a cyclobutenedione derivative, represented by the following formula (II)

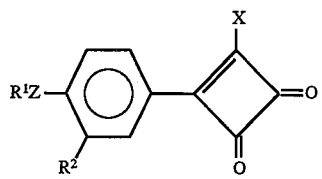

wherein Z represents an oxygen atom or a sulfur atom; $R^1$ represents an alkyl group (preferably having 1 to 18 carbon atoms, more preferably 1 to 12 carbon atoms), an alkenyl group (preferably having 1 to 18 carbon atoms, more preferably 1 to 12 carbon atoms), or an alkynyl group (preferably having 1 to 18 carbon atoms, more preferably 1 to 12 carbon atoms) ; $R^2$ represents a hydrogen atom, an alkyl group (preferably having 1 to 12 carbon atoms, more preferably 1 to 6 carbon atoms), an alkenyl group (preferably having 1 to 12 carbon atoms, more preferably 1 to 6 carbon atoms), or an alkynyl group (preferably having 1 to 12 carbon atoms, more preferably 1 to 6 carbon atoms); and X represents a chlorine atom, a bromine atom, a methoxy group, an ethoxy group or a propyloxy group, with the proviso that $R^1$ and $R^2$ may be connected to each other to form a methylene chain —$(CH_2)_n$— (in which n represents an integer 1 to 10), and the hydrogen atom(s) in $R^1$ may be substituted by a halogen atom, an alkyloxy group (preferably having 1 to 12 carbon atoms, more preferably having 1 to 6 carbon atoms) or a cyano group.

The third aspect of the present invention is a process for the preparation of a cyclobutenedione derivative represented by formula (I) defined above, which comprises reacting a cyclobutenedione derivative represented by formula (II) defined above with an asymmetric 1-amino-2-propanol represented by the following formula (III)

wherein C* represents an asymmetric carbon atom.

The fourth aspect of the present invention is a nonlinear optical element, prepared from a cyclobutenedione derivative represented by formula (I) defined above.

BRIEF DESCRIPTION OF THE DRAWING

By way of example and to make the description more clear, reference is made to the accompanying drawing in which:

The attached figure is a block diagram illustrating an optical system for measuring the optical nonlinearity (SHG activity) of a sample.

DETAILED DESCRIPTION OF THE INVENTION

The inventors made studies of organic compounds suitable for use in nonlinear optical element, including the previously proposed cyclobutenedione derivatives. As a result, it has been found that the cyclobutenedione derivative represented by the foregoing formula (I) has a high solvent solubility and thus can easily grow as a single crystal. It has also been found that the cyclobutenedione derivative of formula (I) has a low melting point (e.g., 190° C. to 210° C.) and thus can easily be melt-processed. Thus, the cyclobutenedione derivative of formula (I) has been found to be superior to the previously proposed cyclobutenedione derivatives and the present invention has been worked out.

The cyclobutenedionyl group contained in the cyclobutenedione derivative represented by the foregoing formula (I) has a strong interaction with π electron in the compound and thus exhibits a strong electron-withdrawing property due to resonance effect as can be seen in the maximum absorption wavelength (intramolecular charge transfer absorption band) shown in the examples described later. Therefore, the cyclobutenedione derivative represented by the foregoing formula (I) is apt to have a structure in which the molecular is electrically strongly polarized and thus can exhibit a high optical nonlinearity.

Further, the cyclobutenedione derivative of formula (I) comprises an asymmetric carbon atom-containing aminoalcohol incorporated therein as a substituent. This substituent makes it possible to control the molecular orientation in the crystal by its steric structure and hydrogen bond. This substituent also allows a molecule having a large dipole moment to be oriented centrosymmetrically, facilitating the growth of a crystal having a great optical nonlinearity.

The cyclobutenedione derivative of formula (I) can be easily synthesized in a good yield in accordance with the following reaction formula

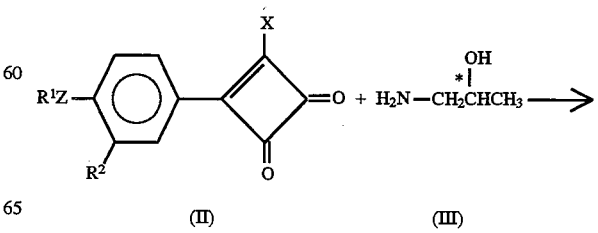

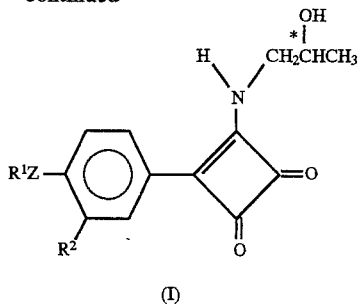

(I)

wherein Z represents an oxygen atom or a sulfur atom; $R^1$ represents an alkyl group, an alkenyl group or an alkynyl group; $R^2$ represents a hydrogen atom, an alkyl group, an alkenyl group or an alkynyl group; and X represents a chlorine atom, a bromine atom, a methoxy group, an ethoxy group or a propyloxy group, with the proviso that $R^1$ and $R^2$ may be connected to each other to form a methylene chain —$(CH_2)_n$— (in which n represents an integer 1 to 10), and the hydrogen atom(s) in $R^1$ may be substituted by a halogen atom, an alkyloxy group or a cyano group.

In some detail, the cyclobutenedione derivative represented by the foregoing formula (II) is first dispersed or suspended in a solvent such as acetone, tetrahydrofuran, dichloromethane, chloroform, methanol, ethanol, N,N-dimethylformamide, N,N-dimethylacetamide and dimethyl sulfoxide. To the resulting solution or suspension is then added gradually asymmetric 1-amino-2-propanol in an amount not less than equal to that of the cyclobutenedione derivative to effect reaction. In general, the reaction rapidly proceeds at room temperature. If necessary, the reaction can be accelerated by heating.

Further, a proper acid binder, that is, a basic compound such as triethylamine, N-methyl morpholine and sodium carbonate may be present in the system to accelerate the reaction. If products are precipitated as the reaction proceeds, they are filtered off. On the other hand, if no products are precipitated, products can be precipitated by concentrating the reaction solution, adding a proper noble solvent thereto, or other means. The resulting crystal can be optionally recrystallized from a solvent such as alcohol and acetone or purified by sublimation.

Instead of the foregoing asymmetric 1-amino-2-propanol, its salt with acid such as hydrochloride, hydrobromide and p-toluenesulfonate may be used as a raw material. It is then reacted with the cyclobutenedione derivative represented by the foregoing formula (II) in the presence of a basic compound such as triethylamine, N-methyl morpholine and sodium carbonate in the same manner as mentioned above to effect synthesis.

The cyclobutenedione derivative represented by the foregoing general formula (II) can also be prepared by subjecting 1,2-dichloro-cyclobutene-3,4-dione and a corresponding alkylphenyl ether, alkylthiophenyl ether or the like to Friedel-Crafts reaction with stirring in a Friedel-Crafts solvent (e.g., carbon disulfide, nitrobenzene, dichloromethane, 1,2-dichloromethane) or by reacting 1,2-dihydroxy-cyclobutene-3,4-dione with a corresponding alkylphenyl ether, alkylthiophenyl ether or the like in the presence of a trialkyloxonium salt in a solvent for halogenation.

The nonlinear optical element of the present invention may be prepared by forming a noncentrosymmetric single crystal of the obtained cyclobutenedione derivatives as described in JP-A-6-82857, or by subjecting the obtained cyclobutenedione derivatives contained in an amorphous polymer to orientation treatment in an electric field to obtain a noncentrosymmetric solid as a nonlinear medium.

The present invention will be further described in the following examples, but the present invention should not be construed as being limited thereto.

EXAMPLE 1

Synthesis of 1-chloro-2-(4-ethoxyphenyl)-cyclobutene-3,4-dione [structural formula (II-1)]

15 g (about 0.1 mol) of 1,2-dichloro-cyclobutene-3,4-dione were dissolved in 40 ml of 1,2-dichloroethane. To the solution were then added 13.3 g (about 0.1 mol) of aluminum chloride. The reaction system was then heated under reflux until it was homogenized. The system was then cooled to a temperature of 0° C. To the system was then added dropwise a solution of 12.2 g (about 0.1 mol) of phenethol (ethyl phenyl ether) in 20 ml of methylene chloride. After the completion of dropwise addition, the reaction mixture was heated under reflux to allow the reaction to proceed.

After the completion of the reaction, the reaction system was cooled. 80 ml of cold water was added to the reaction system. The reaction system was then stirred for 10 minutes. The resulting organic phase was separated, and then dried over anhydrous magnesium Sulfate. The magnesium sulfate was then filtered off. The filtrate was then concentrated until the total amount of the system reached 20 ml. To the system were then added about 50 ml of acetone. The system was then cooled to a temperature of −20° C. The resulting crystal was recovered by filtration, and then dried to obtain 12.4 g of 1-chloro-2-(4-ethoxyphenyl)-cyclobutene-3,4-dione represented by the structural formula (II-1) shown below. The yield was 52%. The product of the structural formula (II-1) exhibited a maximum absorption wavelength ($\lambda$max) of 340.0 nm in the form of methylene chloride solution.

Melting point: 139.4° C. (determined by differential thermal analysis)

Elementary analysis: Calculated %: C 60.89, H 3.81, Cl 15.01 Found %: C 61.08, H 3.95, Cl 14.74

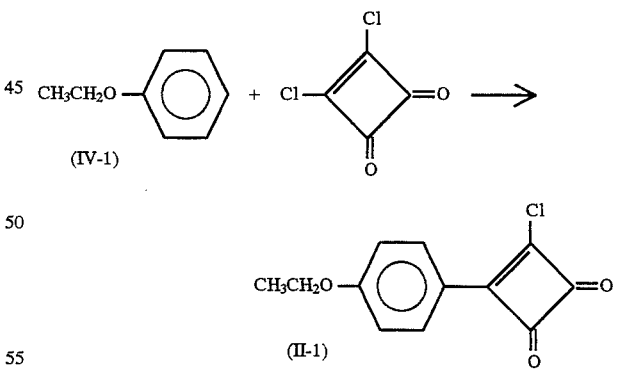

EXAMPLES 2–4

Intermediate products (II-2 to II-4) set forth in Table 1 were synthesized in the same manner as in Example 1 except that as the starting materials there were used phenyl ether or phenyl thioether (V-2 to V-4) set forth in Table 1, respectively. These intermediate products were measured for maximum absorption wavelength ($\lambda$max) in the form of methylene chloride solution. The results are set forth in Table 2.

TABLE 1

| Example No. | Starting material (V) | Intermediate product (II) |
|---|---|---|
| Example 1 | 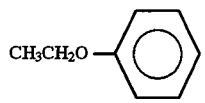 | 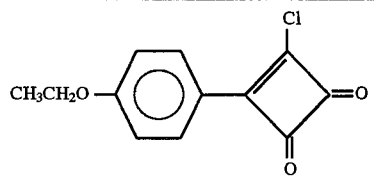 (II-1) |
| Example 2 | CH₃CH₂CH₂O—⌬ | CH₃CH₂CH₂O—⌬—[cyclobutenedione-Cl] (II-2) |
| Example 3 | CH₃CH₂CH₂CH₂O—⌬ | CH₃CH₂CH₂CH₂O—⌬—[cyclobutenedione-Cl] (II-3) |
| Example 4 | CH₃CH₂S—⌬ | CH₃CH₂S—⌬—[cyclobutenedione-Cl] (II-4) |

TABLE 2

| Intermediate product | λmax (nm) | m.p.* (°C.) | Elementary analysis (%) | | | |
|---|---|---|---|---|---|---|
| | | | C | H | Cl | S |
| II-1 | 339.0 | 139.4° C. | 61.08 (60.89) | 3.95 (3.81) | 14.74 (15.01) | — (—) |
| II-2 | 338.9 | 95.6° C. | 62.11 (62.28) | 4.51 (4.39) | 14.04 (14.17) | — (—) |
| II-3 | 342.7 | 64.1° C. | 63.38 (63.52) | 5.20 (4.91) | 13.19 (13.42) | — (—) |
| II-4 | 371.8 | 131.7° C. | 57.01 (57.03) | 3.77 (3.56) | 13.82 (14.06) | 12.33 (12.67) |

*determined by differential thermal analysis (The figures in the parentheses indicate calculated values)

EXAMPLE 5

Synthesis of 1-(4-ethoxyphenyl)-2-[(R)-2-hydroxypropylamino]-cyclobutene-3,4-dione [structural formula (I-1)]

To a solution of 2 g (8.4 mmol) of a compound represented by the following structural formula (II-1) in 40 ml of acetone were added 0.1 g (about 10 mmol) of triethylamine. To the reaction mixture were then added dropwise 1 g (about 13 mmol) of (R)-(-)-1-amino-2-propanol. After the completion of the reaction, the reaction solution was poured into water to precipitate a yellow crystal which was then recovered by filtration to obtain 1.5 g of 1-(4-ethoxyphenyl)-2-[(R)-2-hydroxypropylamino]-cyclobutene-3,4-dione represented by the following structural formula (I-1). The yield was 65%. The elementary analysis of the crystal thus obtained was as follows:

Calculated %: C 64.42, H 6.62, N 4.84

Found %: C 62.89, H 6.89, N 4.59

The product exhibited a melting point of 208° to 210° C. The product exhibited a maximum absorption wavelength (λmax) of 339.5 nm in the form of methanol solution.

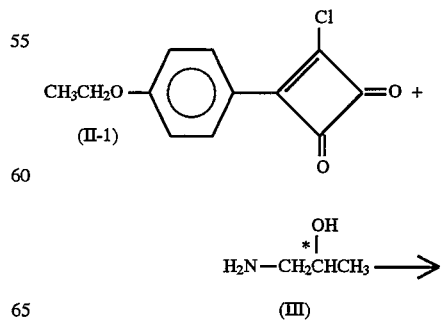

-continued

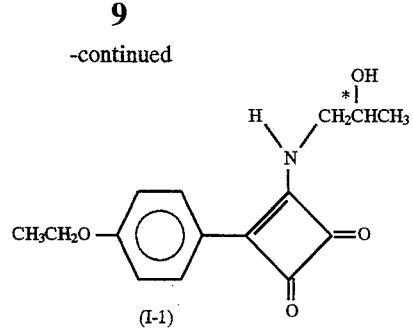

(I-1)

EXAMPLES 6-8

Target products (I-2 to I-4) set forth in Table 4 were synthesized in the same manner as in Example 1 except that as the intermediate products there were used cyclobutenedione derivatives (II-2 to II-4) set forth in Table 3, respectively. These target products were measured for melting point and maximum absorption wavelength (λmax) in methanol solution and subjected to elementary analysis. The results are set forth in Table 4.

TABLE 4

| Target product | UV max (nm) | m.p. (°C.) | Elementary analysis | | | SHG activity |
|---|---|---|---|---|---|---|
| | | | C | H | N | |
| I-1 | 401.6 | 208–210° C. | 62.89 (64.42) | 6.89 (6.62) | 4.59 (4.84) | A |
| I-2 | 340.2 | 204–206° C. | 68.10 (68.33) | 7.87 (7.65) | 8.69 (8.85) | A |
| I-3 | 353.4 | 191–194° C. | 60.22 (61.84) | 7.05 (6.98) | 4.53 (4.62) | A |
| I-4 | 373.6 | 203–206° C. | 61.70 (61.84) | 5.60 (5.88) | 4.73 (4.81) | B |

(Note) SHG activity of 5 to 30 and 1 to 5 were defined as A and B, respectively, relative to SHG activity of urea as 1.

EXAMPLE 9

1-(4-Ethoxyphenyl]-2-[(R)-2-hydroxypropylamino]-cyclobutene-3,4-dione synthesized in Example 5 was packed into a glass cell in the form of powder. When the sample was irradiated with Nd-doped YAG laser (wavelength: 1.064 μm; output: 180 mJ/pulse), it emitted a

TABLE 3

| Example No. | Intermediate product (II) | Target product (I) |
|---|---|---|
| Example 5 | (II-1) | (I-1) |
| Example 6 | (II-2) | (I-2) |
| Example 7 | (II-3) | (I-3) |
| Example 8 | (II-4) | (I-4) | scattered green light of 532 nm as a second harmonic of laser. The intensity of the emission was 5 to 30 times that obtained with an urea sample.

The attached figure is a block diagram illustrating an optical system used in the measurement of optical nonlinearity (SHG activity). Sample 12 was irradiated with light of 1.064 μm from Nd-doped YAG laser 11. A scattered green light of 532 μm emitted by sample 12 was then passed to photomultiplier 16 through lens 13, filter 14 and monochromator 15 to determine the intensity thereof. In the attached figure, 17 and 18 indicate boxcar integrator and oscilloscope, respectively. The optical nonlinearity (SHG activity) of the sample was determined relative to the intensity of an urea powder as a sample. The SHG activity A indicates an activity of from 5 to 30 relative to the urea powder as 1. The SHG activity B indicates a relative activity of from 1 to 5.

EXAMPLE 10

The compounds (I-2 to I-4) obtained in Examples 6 to 8 were used to prepare samples which were then measured for SHG activity in the same manner as in Example 9. The results are set forth in Table 4.

EXAMPLE 11

The compound (I-1) obtained in Example 5 was examined for solubility in organic solvents. The compound (I-1) was dissolved in 100 ml of methanol, acetone and methylene chloride in an amount of 3 g, 2 g and 2 g, respectively, at a temperature of 30° C. to make a uniform solution. On the other hand, the cyclobutenedione derivative represented by the general formula (IV) described in JP-A-3-112950 was dissolved in methanol, acetone and methylene chloride in an amount of as small as 0.3 g, 0.1 g and 0.2 g, respectively, under the same conditions as above.

EXAMPLE 12

The compounds (I-2) to (I-4) obtained in Examples 6 to 8 were examined for solubility in the same manner as above. As a result, the compound (I-4) exhibited about the same solubility as that of the compound (I-1). The compounds (I-2) and (I-3) exhibited a solubility of 3 to 7 times that of the compound (I-1).

In accordance with the present invention, a novel chemical substance suitable for optical organic nonlinear optical element having a high optical nonlinearity and an excellent chemical and thermal stability, workability and transparency and a nonlinear optical element comprising such a chemical substance can be provided.

While the invention has been described in detail and with reference to specific embodiments thereof, it will be apparent to one skilled in the art that various changes and modifications can be made therein without departing from the spirit and scope thereof.

What is claimed is:
1. A cyclobutenedione derivative represented by formula (I)

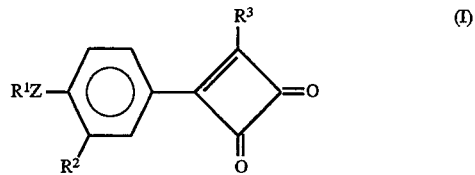

wherein Z represents an oxygen atom or a sulfur atom; $R^1$ represents an ethyl, propyl or butyl group, an alkenyl group or an alkynyl group; $R^2$ represents a hydrogen atom, an alkyl group, an alkenyl group or an alkynyl group, with the proviso that $R^1$ and $R^2$ may be connected to each other to form a methylene chain —$(CH_2)_n$— wherein n represents an integer of 1 to 10, and that the hydrogen atom(s) in $R^1$ may be substituted by a halogen atom, an alkyloxy group or a cyano group; and $R^3$ represents the following substituent

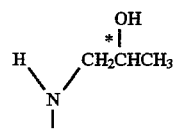

wherein C* represents an asymmetric carbon atom.

2. A nonlinear optical element comprising a cyclobutenedione derivative represented by formula (I)

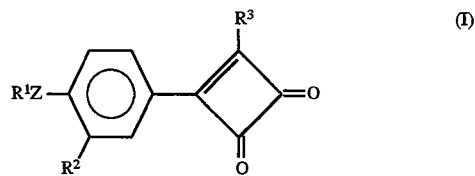

wherein Z represents an oxygen atom or a sulfur atom; $R^1$ represents an ethyl, propyl or butyl group, an alkenyl group or an alkynyl group; $R^2$ represents a hydrogen atom, an alkyl group, an alkenyl group or an alkynyl group, with the proviso that $R^1$ and $R^2$ may be connected to each other to form a methylene chain —$(CH_2)_n$— wherein n represents an integer of 1 to 10, and the that hydrogen atom(s) in $R^1$ may be substituted by a halogen atom, an alkyloxy group or a cyano group; and $R^3$ represents the following substituent

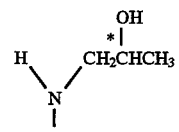

wherein C* represents an asymmetric carbon atom.

* * * * *